United States Patent [19]

England

[11] 4,131,740
[45] Dec. 26, 1978

[54] ALKYL PERFLUORO-ω-FLUOROFORMYL ESTERS AND THEIR PREPARATION

[75] Inventor: David C. England, Wilmington, Del.

[73] Assignee: E. I. Du Pont de Nemours and Company, Wilmington, Del.

[21] Appl. No.: 789,724

[22] Filed: Apr. 20, 1977

[51] Int. Cl.$^2$ .................. C07C 69/34; C07C 69/63
[52] U.S. Cl. .................. 560/180; 560/184; 526/247; 562/586; 562/583
[58] Field of Search .................. 560/197, 184; 260/535 H

[56] References Cited

U.S. PATENT DOCUMENTS

| | | | |
|---|---|---|---|
| 3,114,778 | 12/1963 | Fritz et al. | 260/535 H |
| 3,248,419 | 4/1966 | Hauptschein et al. | 560/197 |
| 3,250,808 | 5/1966 | Moore, Jr. et al. | 560/184 |

OTHER PUBLICATIONS

Ryazanova, M. R. et al. "Synthesis of Fluorides of Monoesters of Dibasic Perfluoro Acids," Zh. Vses. Khim. Obshchest. (1972) 17(3) 347–348, (See Chemical Abstracts 77 (1972) #113,767p.

S(1) – Ryazanova et al. "Monoesters of Perfluorodicarboxylic Acids," (See Chemical Abstracts 79 (1973) #65,819z.

S(2) – Berenblit et al. "Electrochemical Systhesis of Perfluorocarboxylic Acids," (See Chemical Abstracts 82 (1975) #78,455q.

Lovelace, A. M. et al. "Aliphatic Fluorine Compounds," Reinhold Publ. ACS Monograph Series, (1958) pp. 47, 137–138, and 221–222.

Jacques D. et al. "Acid–catalyzed Ether Fission," Journal of the Chemical Society, (1964) pp. 2683–2689.

*Primary Examiner*—James O. Thomas, Jr.
*Assistant Examiner*—Leah Hendriksen

[57] ABSTRACT

Alkyl perfluoro-ω-fluoroformyl esters are provided which have the formula:

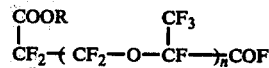

wherein R is alkyl of 1–6 carbon atoms, and n is 0–6 (preferably 0).

Compounds where n is 0 are prepared by contacting $SO_3$ with a compound of the formula ROOC—CF$_2$—CF$_2$—OR$^1$. Compounds where n is 1–6 are prepared by contacting a compound where n is 0 with hexafluoropropylene oxide.

5 Claims, No Drawings

ALKYL PERFLUORO-ω-FLUOROFORMYL ESTERS AND THEIR PREPARATION

BACKGROUND OF THE INVENTION

1. Field of Invention

This invention relates to fluorinated α-carboxylic-ω-carbonyl fluorides and their preparation.

2. Prior Art

Fluoromonomers containing carboxyl or carboxylic ester groups, such as described in U.S. Pat. No. 3,546,186, issued Dec. 8, 1970, have been difficult to prepare. Such monomers are useful in preparing fluorohomopolymers or copolymers with tetrafluoroethylene. Thus, it would be advantageous to be able to prepare fluoromonomers easily.

Symmetrical difluoromalonic compounds of the formula $CF_2Q_2$ where Q may be COOH, COOalkyl or COF are known (E. J. P. Fear et al., J. Appl. Chem., 5, 589-594 (1955); and J. Heicklen, J. Phys. Chem., 70, 618-627 (1966)). Ryazanova et al., Zh. Vses. Khim. Obshchest, 1972, 17, No. 3, 347-8, describe compounds of the formula $ROOC(CF_2)_nCOF$ where n is 3, 4 or 6.

SUMMARY OF THE INVENTION

According to the present invention there is provided a compound of the formula:

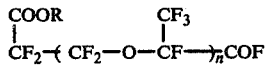

wherein R is alkyl of 1-6 carbon atoms, and n is 0-6.

Also provided is a process for preparing ROOC—$CF_2$—COF comprising: contacting $SO_3$ with a compound of the formula ROOC—$CF_2$—$CF_2$—$OR^1$ wherein R and $R^1$, alike or different, are alkyl of 1-6 carbon atoms.

Further provided is a process for preparing a compound of the formula

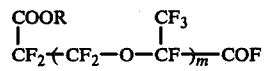

wherein R is alkyl of 1-6 carbon atoms, and m is 1-6, comprising: contacting a compound of the formula ROOC—$CF_2$—COF where R is as defined above with hexafluoropropylene oxide.

DETAILED DESCRIPTION OF THE INVENTION

The compounds of the invention are fluorine-containing α-carboxylic-ω-carbonyl fluorides of the formula

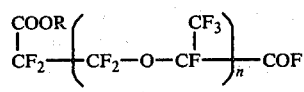

I in which R is alkyl of 1-6 carbon atoms, particularly methyl or ethyl and n is 0-6, preferably 0. The compound $H_3COOC$—$CF_2$—COF is most preferred.

The compounds of the invention where n is 0 are prepared by reacting lower alkyl β-alkoxytetrafluoropropionates (Wiley U.S. Pat. No. 2,988,537) with sulfur trioxide to obtain the corresponding carboalkoxydifluoroacetyl fluorides according to the equation

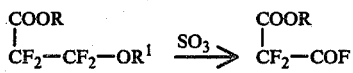

The compounds of formula III are then reacted with hexafluoropropylene oxide to obtain the α-carboxylic-ω-carbonyl fluorides of formula V in which m = 1-6, according to the equation

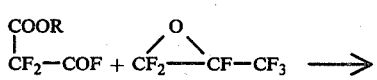

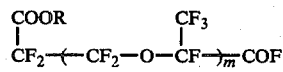

V

The reaction of compounds of formula II with sulfur trioxide is exothermic and provision should be made for dissipating the heat of reaction. One method is to add the alkoxyester compound of formula II in small portions to the $SO_3$ with cooling by reflux condenser or external cooling means. Alternatively, the $SO_3$ can be added in small portions to the alkoxyester, but the former procedure is preferred. The reaction can also be carried out on a continuous basis by slowly feeding the separate reactants into a cooled reaction zone from which product is continuously withdrawn. Sulfur trioxide can be used either in monomeric form or polymeric form. The reaction is preferably carried out neat. However, it can be operated also in the presence of diluents which are relatively inert to $SO_3$ or which couple with $SO_3$, e.g., dioxane, chloroform, carbon tetrachloride, fluorocarbon liquids and the like. Temperatures at which the reaction is operable range from about $-30°$ C. to about 250° C. and temperatures from about 0-100° C. are preferred. Pressure is not a critical variable and pressure both below and above atmospheric pressure can be employed. The molecular proportions in which $SO_3$ and the compounds of formula II can be brought together to carry out this reaction can be varied widely such as from about 1:20 to 20:1, preferably about 2 to 1.

The reaction of a compound of formula III with hexafluoropropylene oxide is preferably carried out in the presence of fluoride ion as a catalyst. This is readily accomplished by using a suitable fluoride, e.g., an alkali metal fluoride such as cesium fluoride, potassium fluoride; silver fluoride; ammonium fluoride; a tetraalkylammonium fluoride (alkyl of 1-4 carbons) such as tetramethylammonium fluoride, tetraethylammonium fluoride, and tetrabutylammonium fluoride, and sulfonium fluorides such as benzene sulfonium fluoride. The fluoride catalyst is usually used in conjunction with an inert liquid diluent (preferably an organic liquid) in which the selected fluoride is at least 0.001% soluble. The fluoride catalyst may be used in amounts from about 0.001 to about 1.0 molar equivalent per mole of the compound of formula III. Suitable diluents include ethylene glycol dimethyl ether, diethylene glycol dimethyl ether, tetraethylene glycol dimethyl ether, and aprotic solvents such as acetonitrile. The reaction is somewhat exothermic and provision for dissipation of the heat of reaction should be made. Temperatures employed can range from about $-50°$ C. to about $200°$ C. with temperatures in the range of about $-10$ to about $80°$ C. being preferred. Pressure is not a critical variable and pressures both below and above atmospheric pressure are operable. Hexafluoropropylene oxide is a gas over much of the operable temperature range and pressures close to atmospheric pressure are preferred. Operable molar proportions of hexafluoropropylene oxide to the compounds of formula III can vary from about 1:20 to about 20:1, preferably about 1 to 1.

As illustrated in the examples, more than one mol of hexafluoropropylene oxide can react with a compound of formula III to yield compounds of formula V in which m is greater than one. To obtain products with higher values of m, higher molecular proportions of hexafluoropropylene oxide are employed and higher pressures and lower temperatures are selected. To obtain products with lower values of m (e.g. 1 or 2) higher molecular proportions of the compound of formula III are employed and lower pressures and higher temperatures are selected.

Each of the compounds of formula I is a reactive organic compound which is at once a carboxylic ester and an acid fluoride. Such fluorinated compounds are rare, and understandably so because the known processes for synthesizing difunctional carboxylic compounds readily yield dicarboxylic esters as well as diacid fluorides but teach almost nothing about how to obtain compounds with both a carboxylic ester group and a carbonyl fluoride group in the same molecule. In carrying out reactions with compounds of formula I care must be taken to prevent their ready conversion to the more ordinary corresponding dicarboxylic esters or dicarbonyl fluorides.

Compounds of formula I are useful as intermediates in the preparation of new fluorine-substituted polymerizable olefinic compounds containing carboxylic acid or ester groups. As shown in the examples, the compounds of formula I in which n = 0 can be reacted with hexafluoropropylene oxide in the presence of fluoride ion catalyst to prepare the compounds of formula I in which n is 1 to 6, e.g., the compounds of formula V. In turn the compounds of formula V can be pyrolyzed over a solid basic salt such as sodium phosphate, sodium carbonate or potassium carbonate at moderate temperatures to obtain the corresponding polymerizable monomers of formula VI according to the equation $$\begin{array}{c} \text{COOR} \quad \text{CF}_3 \\ | \quad\quad\quad | \\ \text{CF}_2\text{-}(\text{CF}_2\text{OCF})_m\text{-COF} \end{array} \xrightarrow{\Delta}$$

V

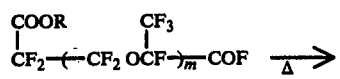

VI (p is 0 to 5, e.g., m−1)

As illustrated in the examples, the monomers of formula VI can be homopolymerized to heavy oils suitable as lubricants and can be copolymerized, for example, with tetrafluoroethylene or chlorotrifluoroethylene, to yield tough, solid polymers which are thermoplastic and capable of being hot pressed or rolled into sheets and films for wrapping uses, as protective layers where exceptional chemical stability is required and as ion exchange membranes in electrolysis cells.

These polymers may be represented by the repeating unit

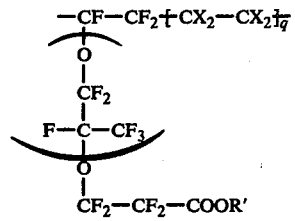

in which p is 0 to 5, q is 0 to 20, the X's may be all fluorine or three fluorine and one chlorine and R' is H or lower alkyl. The preferred copolymers have average compositions corresponding to those in which p is 1 or 2 and q is 1 to 9.

In the examples which follow parts are by weight unless otherwise specified.

EXAMPLE 1

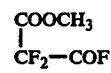

Sulfur trioxide (40 ml) was added to a 3-neck flask attached to a still and fitted with a dropping funnel and thermometer. Crude $CH_3OCF_2CF_2COOCH_3$ (100 g) was added dropwise from the funnel to the magnetically stirred sulfur trioxide at a rate to maintain a gentle reflux due to the exothermic reaction. When addition was complete, the mixture was distilled at atmospheric pressure. Product distilling at $82-86°$ C. was shown by gas chromatographic analysis to contain about 69.5 g of $H_3COOC-CF_2-COF$ (85%) and the remainder mostly $CH_3OSO_2F$. This mixture was passed over sodium fluoride pellets at about $400°$ C./4 mm, converting the $CH_3OSO_2F$ to $CH_3F$ and $NaOSO_2F$. Pure $H_3COOC-CF_2-COF$ was then isolated by distillation.

EXAMPLE 2

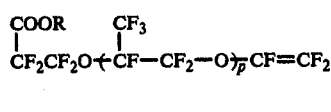

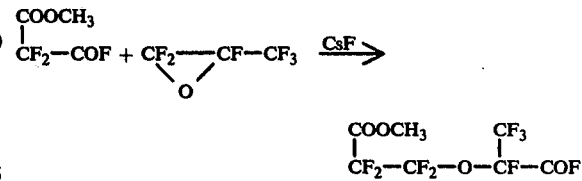

In a 250 ml glass flask fitted with a dry ice condenser and ports for addition of gases, liquids and solids, was placed 20 ml of tetraglyme (tetraethyleneglycol dimethyl ether), 6.0 g CsF and 26.3 g crude $H_3COOCCF_2COF$ (containing 3% $CH_3OSO_2F$). With the mixture kept below $15°$ C., 29.2 g of hexafluoropropylene oxide (HFPO) was slowly added. Upon completion of the reaction, excess $H_3COOCCF_2COF$ and HFPO were removed under vacuum at $40°$ C. The residue was distilled and crude $H_3COOC-CF_2-CF_2-O-CF(CF_3)-COF$ distilled at $75°-95°$ C./400 mm. Its structure was confirmed by:

IR (liq): 1900, 1820, 1330, 1250, 1140, 1035 cm$^{-1}$
PMR (CCl$_4$): 4.04 ppm (singlet)
FMR (CCl$_4$): +21.6 (multiplet, 1F), −82.4 (broad mult., 4F), −86.3 (mult., 1F), −119.8 (mult., 2F), −130 ppm (mult., 1F)

EXAMPLE 3

A 150 ml Carius tube was loaded with a mixture of 0.5 g each of CsF and KF (vacuum dried at 400° C.), 3 ml tetraglyme, 34.5 g H$_3$COOC—CF$_2$—COF and 60 g HFPO. The tube was sealed and rotated overnight at room temperature. Distillation of the reaction mixture yielded 15 g H$_3$COOC—CF$_2$—CF$_2$—O—CF(CF$_3$)-COF, b.p. 65° C./100 mm.

Anal. Calcd. for C$_7$H$_3$F$_9$O$_4$: C, 26.10; H, 0.94; F, 53.09; Found: C, 25.87; H, 0.89; F, 53.34.

EXAMPLE 4

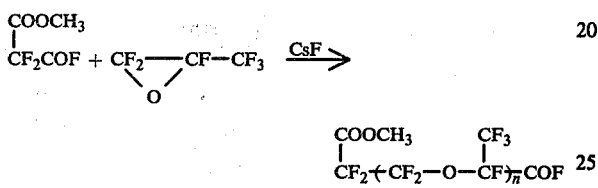

Powdered cesium fluoride (15 g) was placed in a 500 ml 4-necked flask, which was then plugged except for a connection to a manifold attached to a vacuum pump and open-end manometer. Vacuum was applied to the flask while it was heated with a Meeker burner to thoroughly dry the cesium fluoride. After the flask had cooled, dry nitrogen was admitted and then a large magnetic stirrer. The flask was fitted with a thermometer, reevacuated, filled with nitrogen and 20 ml of tetraglyme and 63 g (0.4 m) of H$_3$COOCCF$_2$COF added. The flask was then cooled to −10° C., evacuated and filled to 600 mm pressure with hexafluoropropene epoxide (HFPO) three times. Stirring was started and the pressure of HFPO was maintained automatically at 600 mm by a vacuum regulator. The HFPO was absorbed steadily in an exothermic reaction and cooling was necessary to keep the temperature between 0° and −10° C. The reaction was stopped after 140 g (0.84 m) of HFPO had been absorbed.

The low layer (190 g) was distilled. The products obtained are tabulated below. The ratio of products formed can be varied by the temperature of reaction and mainly by the amount of HFPO used.

| | | | PRODUCTS | | | | | |
|---|---|---|---|---|---|---|---|---|
| | | | Empirical | ANALYSES | | | | |
| | | | | %C | | %H | | %F | |
| Formula n = | b.p. ° C/mm | wt. (g) | Formula | Calcd. | Fd. | Calcd. | Fd. | Calcd. | Fd. |
| 1 | 69/100 | 11.8 | C$_7$H$_3$F$_9$O$_4$ | 26.10 | 25.87 | 0.94 | 0.89 | 53.09 | 53.34 |
| 2 | 106/100 | 14.9 | C$_{10}$H$_3$F$_{15}$O$_5$ | 24.61 | 24.65 | 0.62 | 0.74 | 58.39 | 58.49 |
| 3 | 57/0.3 | 31.3 | C$_{13}$H$_3$F$_{21}$O$_6$ | 23.87 | 24.07 | 0.46 | 0.61 | 60.99 | 60.72 |
| 4 | 80/0.2 | 42.5 | C$_{16}$H$_3$F$_{27}$O$_7$ | 23.43 | 23.78 | 0.37 | 0.48 | 62.55 | 62.40 |
| 5 | 85/0.2 | 24.8 | C$_{19}$H$_3$F$_{33}$O$_8$ | 23.14 | 23.51 | 0.31 | 0.52 | 63.58 | 63.29 |
| 6 | 107/0.5 | 5.7 | | | | | | | |

EXAMPLE 5

The procedure of Example 4 was repeated except that 182 g (1.17 m) of H$_3$COOCCF$_2$COF was used, no cooling was used (run at 55° C.) and the addition of HFPO was stopped after 190 g had been absorbed.
In the distillation, 100 g of H$_3$COOCCF$_2$COF was recovered and the products obtained were 87.5 g (0.27 m, 23%) of the product where n = 1, 40 g (0.08 m, 7%) of the product where n = 2 and 10 g (0.015 m, 1.3%) of the product where n = 3.

EXAMPLE 6

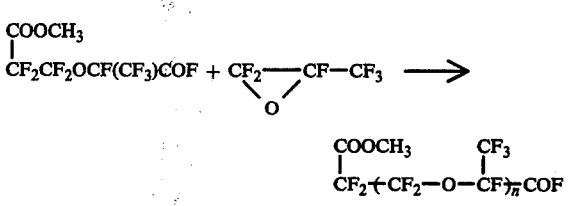

Using the apparatus and general procedure of Example 4, the reaction of 15 g of CsF, 20 ml tetraglyme, 234 g of H$_3$COOCCF$_2$CF$_2$OCF(CF$_3$)COF and 63 g HFPO was carried out at 68° C. Distillation yielded 38 g (0.08 m, 11%) of the above product where n = 2 and 6 g (0.01 m, 1%) of the product where n = 3.

UTILITY EXAMPLE A

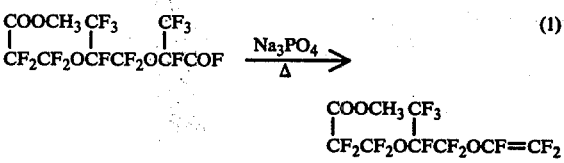

Into the top of a vertically mounted quartz tube 1 inch in diameter and 12 inches long containing 90 cc of fine granules of sodium phosphate (predried at 400° C.) stirred by a motor driven stainless steel screw in the center, the granules heated to 235°–240° C. by an external split-type furnace, was passed 6.4 g of H$_3$COOCCF$_2$CF$_2$OCF(CF$_3$)CF$_2$OCF(CF$_3$)COF along with a slow current of nitrogen over a period of 9 minutes. Off-vapors from the bottom of the tube were condensed and collected in a Dry Ice-acetone cooled trap. The liquid product was distilled to obtain 3.7 g (67%) of methyl 3-[2-(trifluoroethenoxy)-1-(trifluoromethyl)trifluoroethoxy]tetrafluoropropionate, b.p. 98° C./110 mm.

Anal. Calcd. for C$_9$H$_3$F$_{13}$O$_4$: C, 25.61; H, 0.72; F, 58.51; Found: C, 25.47; H, 0.81; F, 59.87.

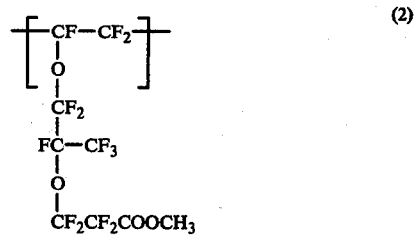

(2)

A glass tube containing 2 g of methyl 3-[2-(trifluoroethenoxy)-1-(trifluoromethyl)trifluoroethoxy]tetrafluoropropionate and 0.01 ml of a 6% solution of perfluoropropionyl peroxide in 1,1,2-trichlorotrifluoroethane was sealed under vacuum and rotated overnight at room temperature. Removal of unreacted monomer under vacuum left 0.5 g of oily homopolymer having a repeating unit of the above formula.

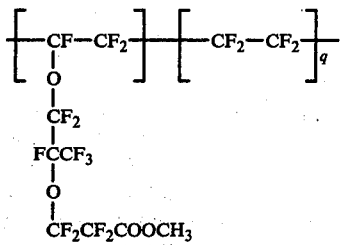
(3)

A glass tube containing 6 g of methyl 3-[2-(trifluoroethenoxy)-1-(trifluoromethyl)trifluoroethoxy]tetrafluoropropionate, 1 g tetrafluoroethylene and 0.01 ml of a 6% solution of perfluoropropionyl peroxide in 1,1,2-trichlorotrifluoroethane was sealed under vacuum at liquid nitrogen temperature and then rotated at room temperature overnight. The mixture became very viscous. Remaining tetrafluoroethylene was bled off and an additional 5 g of tetrafluoroethylene and 0.01 ml of the perfluoropropionyl peroxide solution was sealed into the tube. The tube was rotated for 5 hours at room temperature and then opened. Removal of volatiles at 100° C. under vacuum left 0.6 g of elastomeric copolymer of the above repeating unit where q is greater than 1.

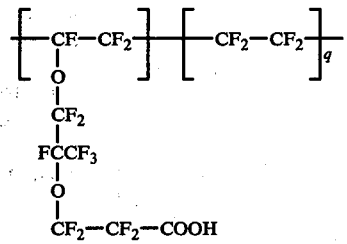
(4)

A 20 ml Carius tube containing 6.8 g (0.016 m) of methyl 3-[2-(trifluoroethenoxy)-1-(trifluoromethyl)trifluoroethoxy]tetrafluoropropionate, 1.7 g (0.017 m) of tetrafluoroethylene, 2 ml of 1,1,2-trichlorotrifluoroethane and 0.01 ml of a 6% solution of perfluoropropionyl peroxide in 1,1,2-trichlorotrifluoroethane was sealed at liquid nitrogen temperature, rotated at room temperature overnight and then opened. The solid product was separated by filtration and washed with ether to obtain 1.7 g of elastomeric copolymer.

The copolymer was pressed at 250° C. under 500 psi to yield a 3 mil film which showed strong infrared absorption for ester carbonyl at 5.5μ. This film was heated for 3 hours at 100° C. in a solution of 15 g KOH in 35 g water and 35 g dimethylsulfoxide (DMSO). Infrared examination of the resulting film showed the ester carbonyl band had been replaced by carboxylic acid absorption (broad at 2.8μ for —OH and at 5.95μ for C=O). This confirmed that a copolymer of the above repeating unit where q is greater than 1 was obtained.

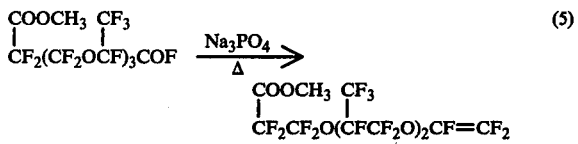
(5)

Using the apparatus and general procedure of Example A(1) above, 22 g of H₃COOCCF₂[CF₂OCF(CF₃)]₃COF was passed slowly with nitrogen over Na₃PO₄ at 235°-240° C. Distillation of the collected product yielded 12 g (61%) of methyl 3-[2-(2-[trifluoroethenoxy]-1-[trifluoromethyl]trifluoroethoxy)-1-(trifluoromethyl)-trifluoroethoxy]tetrafluoropropionate, b.p. 71° C./5.5 mm.

Anal. Calcd. for $C_{12}H_3F_{19}O_5$: C, 24.50; H, 0.51; F, 61.38 Found: C, 24.28; H, 0.68; F, 61.44

UTILITY EXAMPLE B

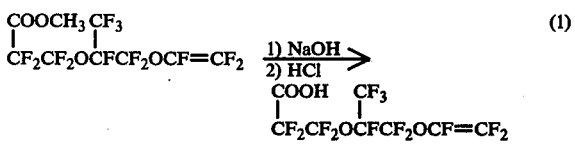
(1)

In a separatory funnel 15 g of crude H₃COOCCF₂CF₂OCF(CF₃)CF₂OCF=CF₂ was shaken with 25 ml of 10% aqueous NaOH at room temperature. The aqueous layer was separated and acidified with cold concentrated HCl. The lower layer which separated was distilled from a little P₂O₅ to obtain 10.7 g of 3-[2-(trifluoroethenoxy)-1-(trifluoromethyl)trifluoroethoxy]tetrafluoropropionic acid, b.p. 53° C./0.25 mm, $n_D^{25}$ = 1.3078.

Anal. Calcd. for $C_8HF_{13}O_4$: C, 23.54; H, 0.25; F, 60.53; Neut. Eq., 408. Found: C, 23.80; H, 0.52; F, 61.71; Neut. Eq., 407.7.

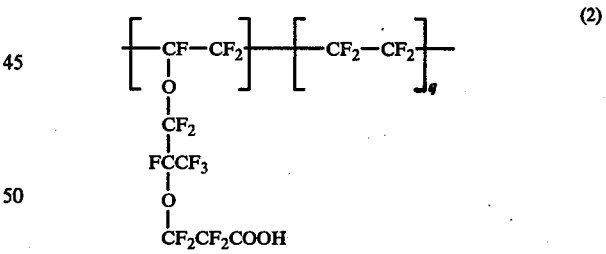
(2)

A glass tube containing 8.8 g of 3-[2-(trifluoroethenoxy)-1-(trifluoromethyl)trifluoroethoxy]tetrafluoropropionic acid, 2.2 g tetrafluoroethylene, 13 ml 1,1,2-trichlorotrifluoroethane and 0.01 ml of a 6% solution of perfluoropropionyl peroxide in 1,1,2-trichlorotrifluoroethane was sealed and rotated at room temperature for 60 hours. Gases were bled off and 3 g tetrafluoroethylene and 0.01 ml of a 6% solution of perfluoropropionyl peroxide in 1,1,2-trichlorotrifluoroethane were added. The tube was sealed, rotated overnight at room temperature and then opened. Filtration and washing in ether yielded 2.3 g of copolymer of the repeating unit indicated above where q is greater than 1. A pressed film showed strong infrared absorption for —COOH.

UTILITY EXAMPLE C

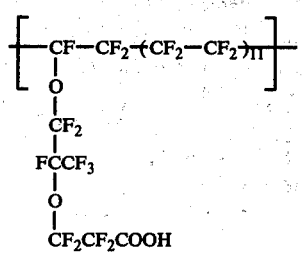
(1)

Using the general procedure of Example A(4), six 20 ml Carius tubes were each charged with 0.01 ml of a 6% solution of perfluoropropionyl peroxide in 1,1,2-trichlorotrifluoroethane and the respective quantities of methyl 3-[2-(trifluoroethenoxy)-1-(trifluoromethyl)trifluoroethoxy]-tetrafluoropropionate (vinyl ether), tetrafluoroethylene (TFE) and 1,1,2-trichlorotrifluoroethane (solvent) indicated in the table below. The tubes were sealed at liquid nitrogen temperature, rotated at room temperature overnight, cooled and opened. The respective amounts of copolymer were recovered by filtration, washed with ether and dried.

| Tube | Vinyl Ether (s) | TFE (g) | Solvent (ml) | Copolymer (g) |
| --- | --- | --- | --- | --- |
| A | 30.4 | 7.2 | 0 | 2.45 |
| B | 19.5 | 4.6 | 4 | 2.31 |
| C | 18 | 5 | 5 | 3.01 |
| D | 19 | 5 | 4 | 3.55 |
| E | 12.9 | 3 | 12 | 2.9 |
| F | 12.8 | 3 | 8 | 2.8 |

The six copolymer products were combined and a film was pressed at 360° C./20,000 psi. After hydrolysis in KOH-H₂O-DMSO as in Example A(4) the copolymer was shown to have a neutral equivalent of 1500, confirming that the copolymer had the average composition represented by the formula above.

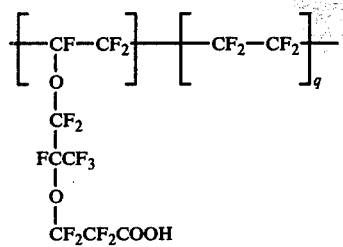
(2)

A glass tube containing 8.8 g of 3-[2-(trifluoroethenoxy)-1-(trifluoromethyl)trifluoroethoxy]tetrafluoropropionic acid, 2.2 g tetrafluoroethylene, 13 ml 1,1,2-trichlorotrifluoroethane and 0.01 ml of a 6% solution of perfluoropropionyl peroxide in 1,1,2-trichlorotrifluoroethane was sealed and rotated at room temperature for 60 hours. Gases were bled off and 3 g tetrafluoroethylene and 0.01 ml of a 6% solution of perfluoropropionyl peroxide in 1,1,2-trichlorotrifluoroethane were added. The tube was sealed, rotated overnight at room temperature and then opened. Filtration and washing in ether yielded 2.3 g of copolymer of the repeating unit indicated above where q is greater than 1. A pressed film showed strong infrared absorption for —COOH.

UTILITY EXAMPLE D (1) — Titration of 12.671 g (0.031 m) of 3-[2-(trifluoroethenoxy)-1-(trifluoromethyl)trifluoroethoxy]tetrafluoropropionic acid to a neutral end point (phenolphthalein indicator) with 15.54 ml of 0.2N sodium hydroxide indicated a neutral equivalent of 407.69 (Calcd. 408). An excess of 1 ml of 0.2N NaOH was added and the solution frozen in a 50 ml Carius tube. Then a solution of 0.25 g ammonium persulfate in 10 ml water, a solution of 0.2 g Na₂S₂O₃.5H₂O in 10 ml water and 3.1 g tetrafluoroethylene were added separately with freezing before sealing the tube. The tube was rotated overnight at room temperature to obtain a clear solution and a little solid polymer. The solution was filtered and acidified to give a gel which was mostly soluble in ether. Removal of ether and drying at 100° C. under vacuum gave 3.2 g of copolymer from which a film was pressed at 100° C./10,000 psi. The copolymer absorbed strongly in the infrared for —COOH (broad 3μ and 5.7μ).

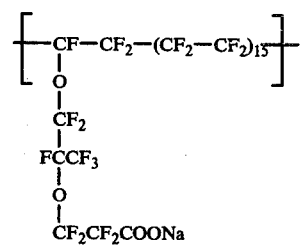
(2)

Using the general procedure of Example D(1) a 200 ml Carius tube containing 6 g (0.015 m) of 3-[2-(trifluoroethenoxy)-1-(trifluoromethyl)trifluoroethoxy]tetrafluoropropionic acid neutralized with a slight excess of 0.2N sodium hydroxide, 0.25 g ammonium persulfate in 10 ml water, 0.02 g Na₂S₂O₃.5H₂O in 10 ml water and 10 g tetrafluoroethylene was rotated overnight at room temperature and then cooled and opened. A gellike polymer (sodium salt) was collected by filtration and vacuum dried at 100° C. to give 6.5 g of copolymer of the average composition indicated by the above repeating unit (neutral equivalent by titration 1976). The filtrate was acidified to give an acid copolymer which was collected by filtration and vacuum dried at 100° C. (wt. 5.8 g).

What is claimed is:

1. A compound of the formula:

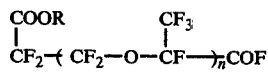

wherein R is alkyl of 1-6 carbon atoms, and n is 1-6.

2. The compound of claim 1 wherein R is methyl or ethyl.

3. A process for preparing a compound of the formula

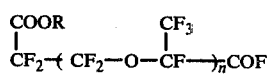

wherein R is alkyl of 1-6 carbon atoms, and m is 1-6, comprising: contacting a compound of the formula ROOC—CF$_2$—COF where R is as defined above with hexafluoropropylene oxide.

4. The process of claim 3 wherein the contacting is carried out in the presence of fluoride ion as catalyst.

5. The process of claim 4 wherein the fluoride ion is from a fluoride compound selected from the group consisting of alkali metal fluorides, ammonium fluoride and tetraalkyl-ammonium fluorides where the alkyl is of 1–4 carbon atoms, said fluoride compound being contained in an inert liquid diluent in which the fluoride compound is partly soluble.

* * * * *